United States Patent
Sun et al.

[11] Patent Number: 6,129,745
[45] Date of Patent: Oct. 10, 2000

[54] MEDICAL DEVICE FOR AUTOMATIC DIAGNOSIS OF UNDERSENSING BY TIMING

[75] Inventors: Weimin Sun, Plymouth; Eric Olson, Minneapolis; John C. Rueter, Shoreview; Michael F. Hess, Minneapolis, all of Minn.

[73] Assignee: Medtronic, Inc., Minneapolis, Minn.

[21] Appl. No.: 09/178,390

[22] Filed: Oct. 23, 1998

[51] Int. Cl.$^7$ .................................................. A61N 1/362
[52] U.S. Cl. ................................................ 607/27; 607/9
[58] Field of Search ............................ 607/4, 9, 27, 28; 600/509, 510

[56] References Cited

U.S. PATENT DOCUMENTS

| | | |
|---|---|---|
| 4,257,423 | 3/1981 | McDonald . |
| 4,374,382 | 2/1983 | Markowitz . |
| 4,556,063 | 12/1985 | Thompson . |
| 5,127,404 | 7/1992 | Wyborny et al. . |
| 5,331,966 | 7/1994 | Bennett . |
| 5,454,836 | 10/1995 | Van Der Veen et al. .................. 607/9 |
| 5,507,782 | 4/1996 | Kieval . |

OTHER PUBLICATIONS

Ventricular Tachycardia & Fibrillation Detection by a Sequential Hypothesis Testin Algorithm (Biomedical Engineering vol. 3 No. Sep. 1990) Thakor, Zhu, Pan.

*Primary Examiner*—George R. Evanisko
*Attorney, Agent, or Firm*—Michael A. Atlass; Harold R. Patton

[57] ABSTRACT

There is provided a system and method applicable for use with a dual chamber pacemaker for determining whether long atrial intervals are due to atrial undersensing or to sick sinus syndrome. The determination of undersensing is based upon an algorithm which statistically analyzes a long atrial interval in terms of the patient's prior atrial rate history, and compares a calculated statistical probability measure with an empirically determined undersense threshold factor. The pacemaker can respond to a determination of undersensing by correcting already collected diagnostic data, adjusting one or more pacemaker operating parameters, adjusting synchronous tracking and/or providing an annotated marker channel for indicating undersense events.

22 Claims, 8 Drawing Sheets

AV Conduction is OK $2^0$ AV Block

Complete AV Block

MEDICAL DEVICE FOR AUTOMATIC DIAGNOSIS OF UNDERSENSING BY TIMING

FIELD OF THE INVENTION

The present invention relates to pacemaker systems and describes how to operate such systems for determining atrial undersensing in order to take corrective action or to compile research, diagnostic or other related information.

BACKGROUND OF THE INVENTION

Dual chamber pacemakers have had an enormous impact on the treatment of individuals with a variety of cardiac conditions. A dual chamber pacemaker capable of operating in a DDD mode can both pace and sense in each of the heart's chambers i.e., in the atrium and in the ventricle. Such a DDD-type dual chamber pacemaker generally requires two leads, an atrial lead for sensing and pacing in the atrium and a ventricular lead for sensing and pacing in the ventricle. The leads connect sense signals back to the pacemaker, and connect stimulus pulses from the pacemaker to the cardiac chamber. Dual chamber pacemakers can also be designed or programmed to operate in a VDD mode, wherein depolarization signals are sensed in both the atrium and the ventricle, but pacing is performed only in the ventricle. Both DDD and VDD modes enable synchronous pacing, i.e., pacing the ventricle in a timed relationship to a sensed atrial signal so as to mimic the heart's natural AV conduction, and thus provide delivery of the ventricular pace pulse at about the time that the ventricle has filled with blood due to the contraction of the atrium. Such synchronous pacing is highly desirable for maximizing cardiac output. Without it, hemodynamic efficiency may be compromised, and other untoward effects may occur.

In both DDD and VDD modes of operation, reliable atrial sensing is critical for maintenance of AV-synchrony and for other desired functions, such as mode switching. A problem that may compromise reliable atrial sensing is that of atrial undersensing, i.e., failure to sense an atrial depolarization signal. Atrial undersensing may arise from a number of different sources, including the patient's activity level, atrial lead dislodgment, improper atrial sensitivity setting, or variations in P-wave amplitude induced by respiration. Of particular importance is placement of the atrial electrode (for unipolar systems) or electrodes (for bipolar systems) with respect to the atrial wall. For 2-lead systems where a separate atrial lead is utilized, a good chronic fixation is generally achieved between the distal tip of the lead and the heart wall, although it is potentially subject to lead dislodgment. With a VDD system, a single pass lead may be used, which has one or two "floating" electrodes positioned on a portion of the lead that is in the atrium. Such an electrode or electrodes are not fixed to the atrial wall and thus are not as efficient in picking up the P-waves. While many techniques have been incorporated into dual chamber pacemaker technology for reliable atrial sensing, the occurrence of undersensing remains a problem, as failure to detect an atrial sense compromises pacemaker response.

It has long been desired in the pacemaker art to implement a pacemaker feature that provides accurate detection of atrial undersensing and that can enable either automatic or programmed adjustments to improve sensing and AV synchrony. One response in the pacemaker industry has been to test for atrial undersensing in a clinical situation, such as during pacemaker follow-up or during trans-telephonic monitoring sessions. In these situations, the clinician observes the ECG and watches for paces that do not synchronize correctly to observed intrinsic cardiac events. However, such observations are limited and may not provide the physician with sufficient information in order to reliably determine whether or not there are episodes of undersensing. Also, such clinical follow-ups are relatively infrequent, and do not provide much opportunity for relatively rapid and efficient response to undersensing conditions.

In contrast to the clinical approach for detecting atrial undersensing, applicant's invention is directed to a new approach for detecting undersensing. It includes a description of a new pacemaker feature and method for operating the pacemaker or other implanted system to enable determination of atrial undersensing based on ongoing monitoring of the patient's atrial rate, or A—A interval. In response to determined undersensing, the pacemaker may store diagnostic information that can be downloaded into an external device for the physician, or may automatically carry on synchronized pacing based on the assumption of undersensing.

SUMMARY OF THE INVENTION

In accordance with the above, this invention may be used to provide a dual chamber pacemaker system and method with an improved capability of testing for and determining whether there is undersensing by an implantable medical device, primarily of atrial depolarizations or contractions.

This invention may also provide a mechanism for more accurately determining atrial event to atrial event intervals. Such better A—A intervals can be used to improve pacemaker effectiveness, provide better information for diagnosis and treatment by whatever means desired.

Additionally, by providing a more accurate basis for knowing what features of electrocardiograms are P-waves, any other application that requires better information regarding the occurrence of P-waves or their detection can become more accurate and useful by employing this invention.

Further, use of this invention may provide a mechanism to improve the likelihood that an implanted device can correctly distinguish between undersensing of atrial events and sick sinus syndrome On the basis of this distinction, such implanted devices can make better use of available information on the occurrence of atrial events to provide better AV synchrony. If desired, the invention can be used to improve the performance of forced AV synchrony pacemaker designs such as is disclosed in U.S. Pat. Nos. 5,441,523 and 5,609,610, both of which are incorporated herein by reference.

Testing for Undersensing (U) and/or Sick Sinus Syndrome (SSS, or S) is suitably combined with an automatic capability for responding on the basis of undersensing so as to optimize AV synchronous operation, and also provides for collection, storage, and reporting of diagnostic information concerning episodes of pacemaker undersensing or patient sick sinus syndrome.

In the system of this invention, testing and determination of atrial undersensing is based upon statistical analysis of a series of atrial intervals (A—A intervals), and performing sequential hypothesis testing.

This invention employs probabilities discovered by application of Hidden Markov Modeling to create a functional mechanism that operates by applying this knowledge in a statistical processing or algorithmic form. In a preferred algorithm utilized by an implantable medical device, such as a pacemaker (or any other device that otherwise has use for sensing atrial events), a series of atrial intervals, which includes a long interval, is examined to test the probability or determine the relative likelihood of atrial undersensing or sick sinus syndrome. We determine undersensing based on the statistics of the atrial intervals(A—A or Atrial to Atrial intervals) generally, and the details are disclosed below. The measured atrial intervals are taken, preferably, during times of no pacing. It is possible to apply these teachings to the ventricular chambers as well if desired, but the initial and presently preferred use is for atrial event timing accuracy. The ratio of the undersensing and sick sinus syndrome probabilities is calculated, based on the means and variances, and compared with empirically chosen thresholds for determination of either undersensing (U) or sick sinus syndrome (SSS). In operation of the preferred algorithm, when a long atrial interval occurs which is approximately twice the mean interval length, or approximately an even multiple of the mean interval, the test is statistically likely to classify the interval as containing an undersensed atrial beat. The mean interval length is updated as a running average for previous atrial interval lengths. The value ranges for thresholds for both U and SSS are chosen to enable a determination of when the ratio reflects that the prolonged interval or intervals are statistically close to reflecting either U or SSS.

In a preferred embodiment, the test for atrial sensing is carried out periodically, the pacemaker being set in a VDD mode so as to enable detection of a series of A—A intervals to provide the required statistical data. Upon determination of undersensing, the pacemaker can respond by going to a control algorithm that assumes undersensing, and delivers a "pseudo-synchronized" (that is, synchronized to the timing of the missing atrial event) ventricular pace pulse following time-out of a preferred A—A interval. The preferred A—A interval may be selected by any suitable means. For example, it can be a simple mean A—A interval based on some predetermined sample A—A interval time out length related to the present pacing rate or to the activity indicated rate, or to the expected normal sinus rates. Alternately, or together with a preferred synchronization routine, test determinations of undersensing or SSS can be stored. These can be downloaded or telemetered out to an external device for later use as diagnostic information or information on the performance of the implanted device. The data on undersensing or sick sinus findings may also be used to initiate automatic adjustment for correcting undersensing, such as by adjusting the atrial sense amplifier sensitivity, or by adjusting some signal enhancement process or device which might be employed by the implanted device itself. (However if sense amplifier sensitivity is increased, a separate procedure must be implemented to provide a check against oversensing).

A passive, non-pacing, or other non therapy-delivering device could employ this invention. Such a device would not require waiting for a period or initiating a period of non-pacing to test the likelihood of undersensing/sick sinus syndrome, because at no time would there be paced intervals or other therapy delivered to confound the measurements of A—A intervals or of the sensing of atrial events generally. Data from a passive device is useful for diagnostic and research purposes as well.

DESCRIPTION OF THE PREFERRED EMBODIMENTS

Figure 1A:
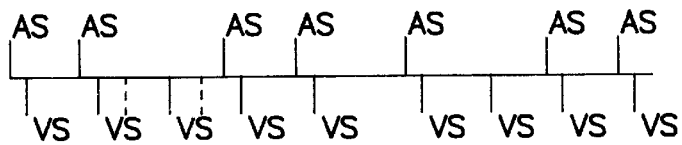
FIG. 1 is a series of three marker channel diagrams, representing respectively first a condition of good A-V conduction, second a condition of second degree A-V block, and third a condition of complete A-V block.

A preferred system for applying this invention would be a pacemaker system incorporating the atrial-undersensing feature of this invention that is suitably made for implanting into a patient who has been determined to suffer from secondary or complete heart block. Such an initial clinical determination can be made by routine marker channel analysis, or by more extensive Holter recording. The clinical data obtained prior to pacemaker implantation may indicate the degree of SSS manifested by long intervals between atrial senses, or it may not. As used herein, SSS means an irregular sinus rhythm, such as results in irregularly spaced longer A—A intervals. Such prior clinical data may be useful in setting certain pacemaker operating conditions, such as amplifier sensitivity. Likewise, the prior clinical history may be useful in judging the relative probability of undersensing (U) or Sick Sinus Syndrome (SSS), along with the probabilities that are determined by the hypothesis testing which is a central feature of this invention.

The sequential hypothesis test of this invention is based on the continual timing of atrial events and determination of probabilities until either a decision threshold for U or SSS is reached, or the data is indeterminate such that neither a hypothesis of U or SSS can be maintained. As set forth in more detail below, the preferred algorithm of this invention determines whether a detected presence of long atrial intervals represents a missed atrial event, thereby indicating undersensing during a normal sinus rhythm (NSR), or an irregular heartbeat indicating SSS. As incorporated into a pacemaker or any other system, the algorithm is continually recording A—A intervals (during times on non-pacing, preferably) that are used to adjust the mean and variance of its A—A interval variables. A determination of undersensing can be responded to automatically by adjustment of pacemaker control to deliver ventricular pace pulses synchronized to presumed missed atrial events, i.e., pseudo-synchronization.

Pseudo-synchronization can be accomplished within the skill of the ordinary artisan in this field, using predetermined A—A or other intervals stored in the implanted device. These intervals (which may be related to pacing rate, and/or other pacing state data) may be modified by particularized therapies that employ various adjustments to AV intervals, or just picked from a look up table or a fixed rate table. It is believed that the use of this invention will require the establishment of a specific algorithm along these lines for each implementation of pseudo-synchronization based on whatever AV synchrony scheme is most easily employed in a particular device. Alternately, or in combination with pseudo-synchronization, the pacemaker may store episodes of determined undersensing or SSS for later use by the clinician, or the device itself, and/or to provide additional marker channel or similar informative outputs to indicate suspected undersensing events on an external electrocardiograph.

We include a brief discussion here of how the Hidden Markov Model approach provides us with the probabilities formulae that allow us to make our determination in this invention of whether we have Normal Sinus Rhythm(NSR), U or SSS conditions. It may be useful to refer to this section and the accompanying FIGS. 6a and 6b to understand the character of Hidden Markov Models applied to this issue.

Figure 6A:
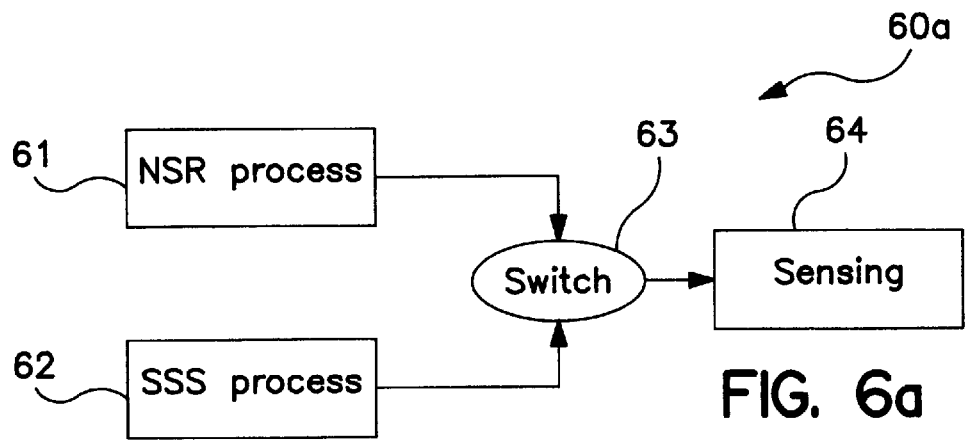
FIG. 6(a) is a block diagram that depicts the sensing of a heart rhythm.

FIG. 6(a) is a block diagram that illustrates sensing of a heart rhythm. Process 61 of this system illustrates a Normal Sinus Rhythm (NRS). Process 62 represents Sick Sinus Syndrome (SSS). The process sensed by Sensing process 64 is dependent on Switch 63, which switches intermittently resulting in some Undersensing (U).

Figure 6B:
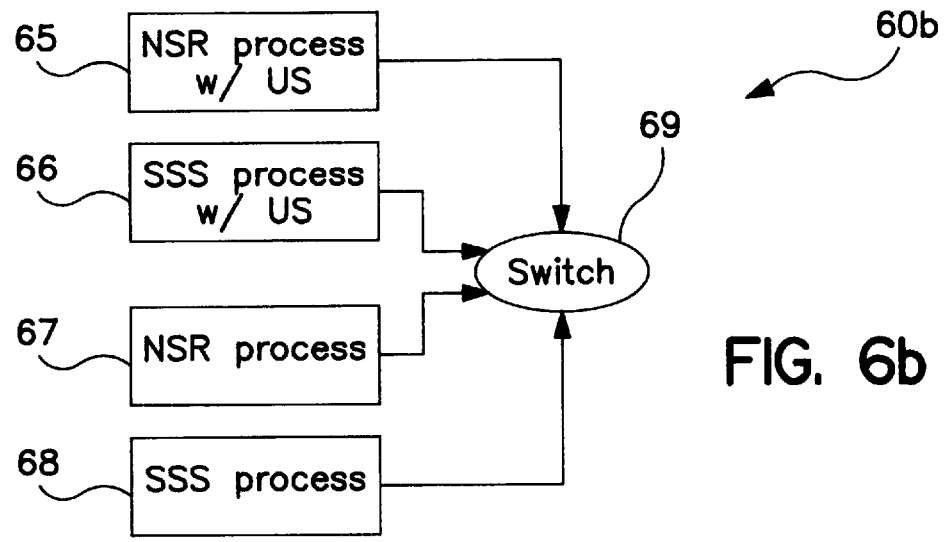
FIG. 6(b) is a block diagram illustrating the four types of sensing situations that may occur when undersensing of the heart rhythm is occurring.

FIG. 6(b) is a block diagram illustrating the four types of sensing situations that may occur when some undersensing of the heart rhythm is occurring within the system of FIG. 6(a). By applying the technique of recursive hypothesis testing to a sequence of events being sensed by this system, it may be determined which type of situation occurred.

Undersensed atrial events will yield a sequence of atrial intervals whose statistics can be used to identify episodes of undersensing. It is assumed that long intervals between atrial senses can result from two causes. The first cause is Undersensing (U), where the interval is long because of a missed event. The other cause is Sick Sinus Syndrome (SSS) where there are no missed events and the interval is actually long due to improperly operating sinus node. We will use the term SSS very loosely in this discussion. For the purpose of this discussion we define SSS to be anything other that Normal Sinus Rhythm (NSR). An interval is considered to be long when the interval length is about twice as long as the mean interval length or longer. If the heart rate is steady and not varying quickly, an undersensed interval must necessarily be approximately twice the mean atrial interval, or a multiple of the mean atrial interval. Since the invention is detecting U, the algorithm will not be executed for intervals less than about twice the mean rate.

If a long interval occurs, it is to be determined whether that interval is NSR with one or more undersensed events, or whether the long interval is really a long interval caused by a SSS-type condition. The sequence of NSR and SSS intervals will be characterized as Gaussian distributions. The probability density of the length of the kth atrial interval A, assuming that it resulted from the state $H_i$, is given by the equation:

$$P(A_k|H_i) = \frac{1}{\sqrt{2\pi\sigma_i^2}} e^{-\frac{(A_k-\mu_i)^2}{2\sigma_i^2}}$$

In this equation, the state $H_i$ is either NSR or SSS. The mean interval length and the variance of the interval length are shown as $\mu$ and $\sigma$, respectively. From these assumptions, we derive a probability ratio of the zeroth (our undersensing hypothesis) to the 1st state(our sick sinus hypothesis) set forth below as equivalent to a probability shown as $F_m$. A description for employing these probability calculations within a programmable device is set forth below.

Figure 1B:
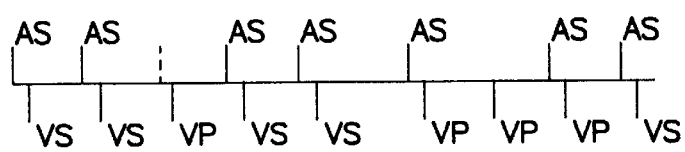
Figure 1C:
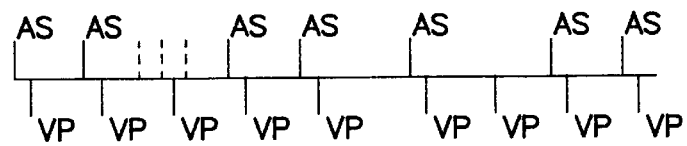

To show the application of this theoretical underpinning to the real world problem, FIGS. 1(a), 1(b) and 1(c) are now discussed.

FIG. 1(a) is a marker channel diagram illustrating good A-V conduction. Each atrial sense (AS) is followed by a ventricular sense (VS), with the time interval between the two events representing a normal AV conduction delay. As illustrated, there are two occurrences where an AS appears to be missing. Since there are two VS events between AS events, it is concluded that the P-wave must have come along in a timely manner, but was not sensed by the pacemaker; the VS was sensed before time-out of the V—V escape interval, such that no ventricular pace pulse (VP) was delivered. In this situation, undersensing can thus be detected from the non-paired VS events.

FIG. 1(b) is a marker channel diagram illustrating second degree A-V block. Second-degree AV block exists, meaning that irregularly the P-wave is not transmitted through the AV node to the ventricle. As shown here, for the same presumed series of P-waves, the atrial marker channel shows the same two long A—A intervals. However, in this case, there is no intervening V sense, so upon time-out of the V—V escape interval, a VP is delivered. However, note that without the premise of second degree A-V block, looking just at the marker channel, there is insufficient information to indicate whether the two long A—A intervals were due to Undersensing or Sick Sinus Syndrome.

FIG. 1(c) is a marker channel diagram illustrating complete A-V block. Complete A-V block exists. Each ventricular event is a VP, and no conduction through to the ventricle is occurring to enable a natural QRS. Again, based just on the marker channel information, it cannot be determined whether two long A—A intervals were the result of U or SSS; while each AS is followed by a VP which is delivered at a timed AV delay following the AS, each VP delivered upon time-out of the ventricular escape interval is not presumed to be synchronized to a P-wave. Thus, the inability to determine whether the Atria have fired (that is, contracted) prevents AV synchrony.

Figure 2A:
FIG. 2(a) is a timing diagram representing a normal sinus rhythm with a steady rate.

Referring now to FIG. 2(a), there is shown a timing diagram of a Normal Sinus Rhythm with a steady rate. That is, each P—P interval is substantially constant.

Figure 2B:
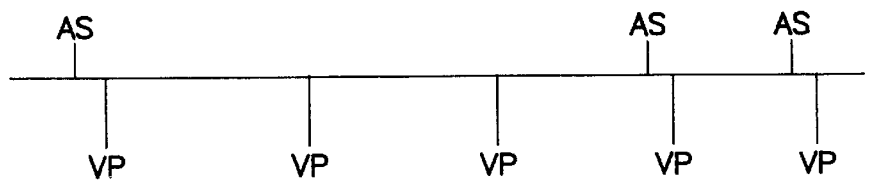
FIG. 2(b) is a marker channel diagram of a conventional pacemaker reacting to the normal sinus rhythm, illustrating a long A—A interval due to undersensing, and ventricular pace pulses delivered in a conventional manner.

FIG. 2(b) is a marker channel diagram illustrating how a current pacemaker operates in the presence of undersensing. After the first AS, a VP is delivered following time-out of the AV interval. However, when the next P-wave is not sensed, the pacemaker times out the V—V escape interval, and then delivers a VP. The next P-wave is again not sensed, or if sensed, comes too early to be tracked such that a third VP is again delivered upon time-out of the V—V escape interval. The next, or fourth, P-wave occurs too early to be sensed during the pacemaker PVARP (that is, Post Ventricular Atrial Refractory Period), and so is ignored. Following this, the next two P-waves are detected, and synchronized VPs can be delivered based on AV interval timing. The net effect of this series is that only five ventricular pace pulses are delivered corresponding to their best hemodynamic timing position relative to the six actual P-waves.

It should be noted that the ventricular sensing information is not required for operation of this invention. This will be clear as its details of operation are explained. It should also become clear that this invention will work with an AAI pacemaker that briefly halts its atrial output to observe intrinsic atrial behavior.

Figure 2C:
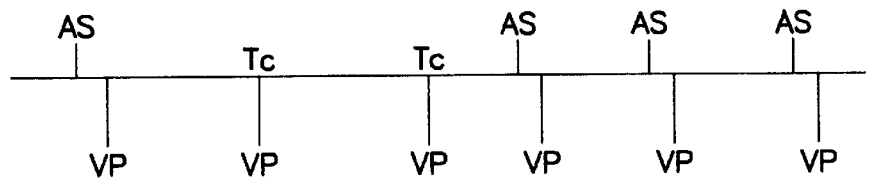
FIG. 2(c) is a marker channel diagram showing an improved ventricular pace response compared to that of FIG. 2(b) based upon a determination of atrial undersensing.

FIG. 2(c) is a marker channel diagram showing a potential response where there has been a determination of undersensing. When the second P-wave is not sensed at the end of the mean A—A interval, the pacemaker times out a confidence interval(Time-out Confidence or $T_c$ interval), which confidence interval takes into account the fact that the missing P-wave may statistically be delayed slightly from the running mean because of the variance. This small variance delay, plus the normal A-V delay, prescribes delivery of a VP at the timed $T_c$. Following this, there is a second undersensed P-wave, and again a VP is delivered at a second time $T_c$. Note that the interval between the second undersensed P-wave and the second $T_c$ is slightly longer, due to compounding of the confidence interval. Thereafter, the fourth P-wave appears and is tracked, as are the next two P-waves. Thus, by the arrangement of FIG. 2(c), six ventricular pace pulses are delivered corresponding to six P-waves. The two VPs following the undersensing are delivered with at least some synchronization with respect to the actual P-waves.

Figure 3:
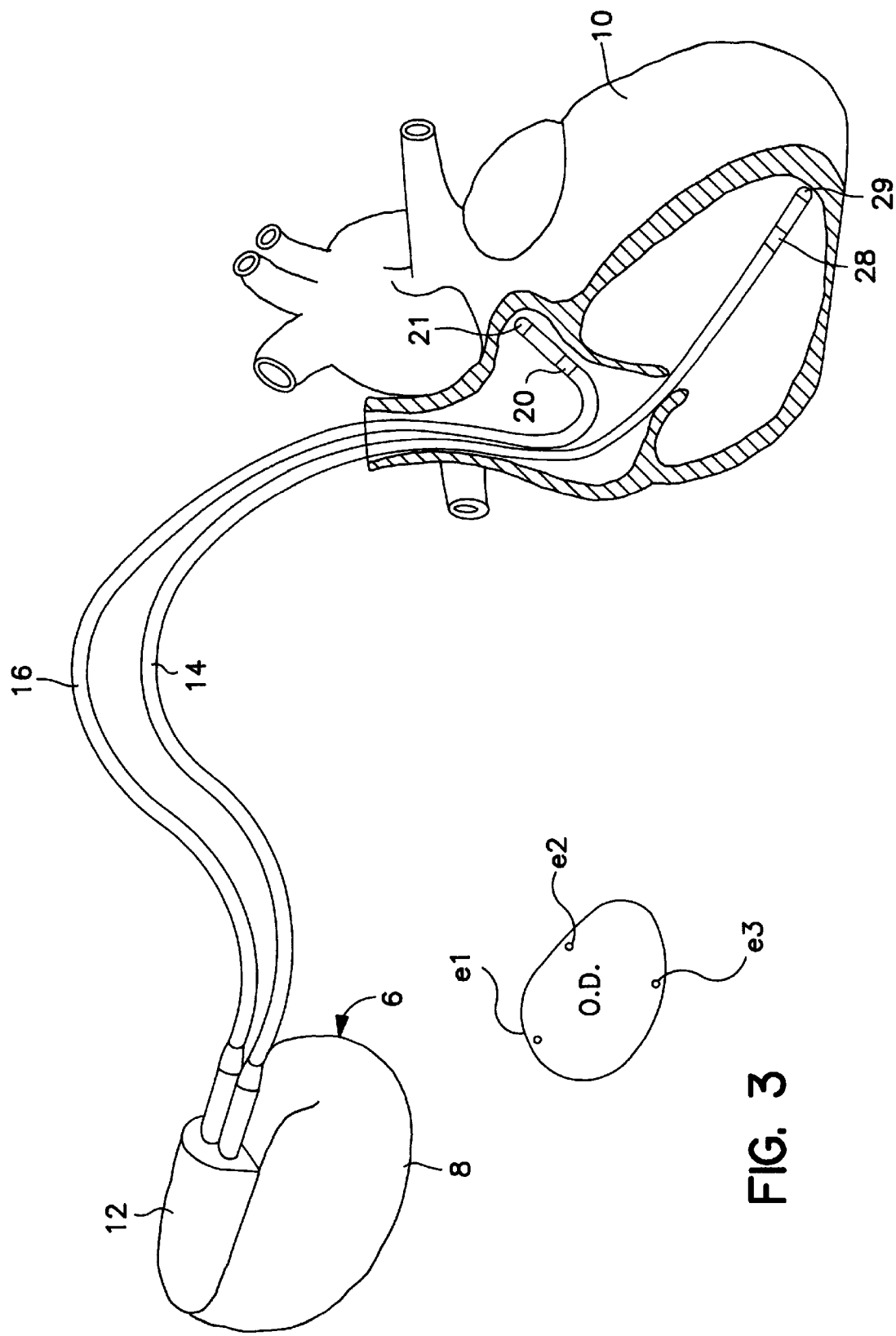
FIG. 3 is an illustration of a dual chamber pacemaker used in accordance with the present invention in conjunction with a pair of pacing leads shown located within a cutaway view of a human heart.

FIG. 3 is a block diagram of a dual chamber pacemaker used in accordance with the present invention in conjunction with an associated set of pacing leads. The leads are illustrated located in a cutaway view of a human heart. A preferred pacemaker is disclosed in U.S. Pat. No. 5,507,782, issued to Kieval et al., incorporated herein by reference in its entirety. FIG. 3 illustrates the external configuration of a typical dual chamber pacemaker 6 used in accordance with Applicants' invention. The pacemaker 6 is provided with a hermetically sealed enclosure 8, typically fabricated of biocompatible metal such titanium. Mounted to the top of the enclosure 8 is a connector block assembly 12, which receives electrical connectors located on the proximal ends of leads 14 and 16. Lead 16 is an atrial pacing lead, carrying two electrodes 20 and 21. Electrodes 20 and 21 are used both to sense atrial depolarizations and to deliver atrial-pacing pulses. Atrial pacing pulses may be delivered between electrode 20 and electrode 21 or between electrode 21 and the housing 8 of the pacemaker 6. Sensing of atrial depolarizations may occur between electrode 20 and electrode 21 or between either of electrodes 20 and 21 and the housing 8 of the pacemaker 6.

Still now referring to FIG. 3, lead 14 represents a ventricular bipolar pacing lead, carrying two electrodes 28 and 29. Discussed above in conjunction with atrial lead 16, electrodes 28 and 29 are used to sense and pace the ventricle. Ventricular pacing may be accomplished between electrodes 28 and 29 or between electrode 29 and the conductive housing 8 of pacemaker 6. Sensing of ventricular depolarizations may be accomplished between electrodes 29 and 28 or between either of electrodes 29 and 28 and the housing 8 of the pacemaker 6. As stated above, leads 14 and 16 may be unipolar, wherein sensing and pacing is done between a single electrode and the pacemaker case. Also, a single pass lead can be used instead of two leads for a VDD system, as is known in the art.

Other apparatus can be used for sensing atrial depolarization that can benefit from this invention, for example, one using a subcutaneous electrode array as is described in Bennett et al, U.S. Pat. No. 5,331,996 (incorporated herein by reference), or one using a single lead in the atrium. Such systems could be used for systems that do not deliver pacing pulses at a desired AV synchrony to atrial contraction.

Figure 4:
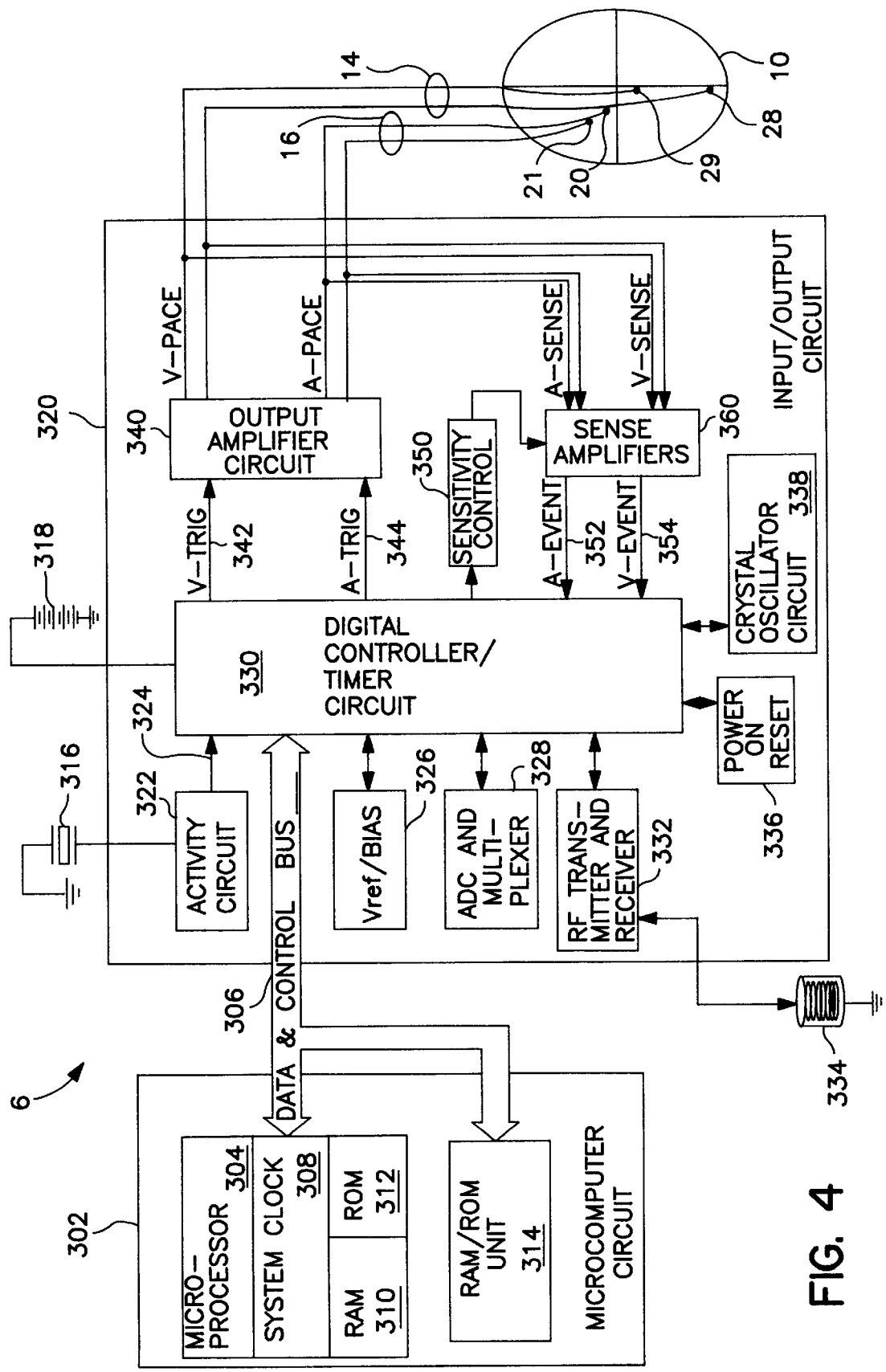
FIG. 4 is a system block diagram of a dual chamber pacemaker illustrating the primary functional components of the pacing system of the current invention.

FIG. 4 is a logic block diagram of an implementation of the pacemaker illustrated in FIG. 3. For heuristic purposes, the current invention is described as being used with a dual chamber pacemaker. It can also be used with external devices, with other implantable devices, or anywhere an atrial sense signal is relevant to the functioning or use of the device OD.

The circuitry illustrated in FIG. 4 resides within the conductive housing 8 of the pacemaker 6. The bipolar leads 14 and 16 are illustrated schematically coupled directly to the circuit. However, of course, in the actual device they would be coupled by means of removable electrical connectors inserted in the connector block 12, illustrated in FIG. 3. Other devices such as OD of FIG. 3 can employ similar circuitry and have electrodes such as e1, e2, and e3 on their surfaces or, if external, on the patient's body. It should also be recognized that the application of this invention is not merely limited to the electrical signal, but to any other representation of a heart beat, which could include mechanical, pressure, sound, oxygen variation, and so forth, any of which have a small variation representing an atrial event and a large variation representing a ventricular event.

Still referring to FIG. 4, the pacemaker is divided generally into a microcomputer circuit 302 and a pacing circuit 320. A pulse generator circuit 340 includes a ventricular pulse generator circuit coupled to the heart 10 by means of electrodes 29 and 28 on lead 14 and an atrial pulse generator circuit coupled to the heart 10 by means of atrial electrodes 20 and 21, located on lead 16. Similarly, pacing circuit 320 includes atrial and ventricular sense amplifiers in sense amplifier circuit 360, coupled to the atrium and ventricle by means of leads 14 and 16. The output circuit 340 and sense amplifier circuit 360 may contain pulse generators and sense amplifiers corresponding to any of those presently employed in commercially marketed cardiac pacemakers. Control of timing and other functions within the pacemaker circuit is provided by digital controller/timer circuit 330, which includes a set of timers and associated logic. Digital controller/timer circuit defines the basic pacing intervals of the device. The microcomputer circuit 302 by means of data and control bus 306 controls the specific values of the pacing intervals. Sensed atrial depolarization are communicated to the digital controller/timer circuit 330 on A event line 352, with ventricular depolarization communicated to the digital controller/timer circuit 330 on V event line 354. In order to trigger generation of a ventricular pacing pulse, digital controller/timer circuit 330 generates a trigger signal on V trig line 342. Similarly, in order to trigger generation of an atrial pacing pulse, digital controller/timer circuit 330 generates a trigger signal on A-Trig line 344. Digital controller/timer circuit 330 also defines time intervals for controlling operation of the sense amplifiers in sense amplifier circuit 360. In addition, digital controller/timer circuit 330 also controls sensitivity settings of the sense amplifiers 360 by means of sensitivity control 350.

In some embodiments of the invention, the dual chamber pacemaker described above may comprise a piezo electric sensor 316, which is intended to monitor patient activity. Similarly, the present invention may be practiced in conjunction with alternate types of rate responsive sensors, or in non-rate responsive pacemakers.

Still referring to FIG. 4, transmission to and from the external programmer (not shown), if included with the pacemaker, is accomplished by means of antenna 334 and associated RF transmitter and receiver 332, which serves both to demodulate received downlink telemetry and to transmit uplink telemetry. For example, circuitry for demodulating and decoding downlink telemetry may correspond to that disclosed in U.S. Pat. No. 4,556,063, issued to Thompson et al, and U.S. Pat. No. 4,257,423, issued to McDonald et al., while uplink telemetry functions may be provided according to U.S. Pat. No. 5,127,404, issued to Wyborny et al., and U.S. Pat. No. 4,374,382, issued to Markowitz. (All these patents with descriptions of telemetry systems are incorporated by this reference). Uplink telemetry capabilities will typically include both the ability to transmit stored digital information as well as the ability to transmit electrocardiograms from either the atrium, or the ventricle, according to the teaching of the above-cited Wyborny patent, as well as transmission of Marker pulses indicating the occurrence of sensed and paced depolarizations in the atrium and ventricle, as disclosed in the cited Markowitz patent. In addition, in the context of the present invention, if intervals between sensed and paced events are measured internally within the pacemaker, these intervals may be encoded in digital form and transmitted via the transmitter 332 and antenna 334 to the external programmer for display and/or analysis.

Crystal oscillator circuit 338 provides the basic timing clock for the circuit, while battery 318 provides power. Power on reset circuit 336 responds to initial connection of the circuit to the battery for defining an initial operating condition and similarly, resets the operative state of the device in response to detection of a low battery condition. Reference mode circuit 326 generates stable voltage reference and currents for the analog circuits within the pacing circuit 320, while analog to digital converter ADC and multiplexor circuit 328 digitize analog signals and voltage to provide real time telemetry of a cardiac signals from sense amplifiers 360, for uplink transmission via RF transmitter and receiver circuit 332. Voltage reference and bias circuit 326, ADC and multiplexor 328, power on reset circuit 336 and crystal oscillator circuit 338 may correspond to any of those presently used in current marketed implantable cardiac pacemakers.

Continuing to refer to FIG. 4, microcomputer circuit 302 controls the operational functions of digital controller/timer 330, specifying which timing intervals are employed, and controlling the duration of the various timing intervals via data and control bus 306. Microcomputer circuitry contains a microprocessor 304 and associated system clock 308, and RAM and ROM circuits 310 and 312, respectively. In addition, microcomputer circuit 302 includes a separate RAM/ROM chip 314. Microprocessor 304 is interrupt driven, operating in a reduced power consumption mode normally, and awakened in response to defined interrupt events, which may include delivery of atrial and ventricular pacing pulses as well as sensed atrial and ventricular depolarizations. In addition, if the device operates a rate responsive pacemaker, a timed interrupt may be provided in order to allow the microprocessor to analyze the output of the activity circuit 322 and update the basic rate interval of the device.

In the context of the present invention, the microprocessor 304 serves to perform the functions of detecting atrial undersensing or sick sinus syndrome, and responding to determined undersensing. The specific test algorithm may be stored in chip 314, and carried out under control of microprocessor 304.

In the pacemaker system and method of this invention, an algorithm is used to test whether a long interval between atrial senses indicates either SSS or U. Successive atrial events are monitored, and the presence of a long interval between atrial senses is assumed to be either sick sinus syndrome or an undersense. A series of atrial intervals containing at least one long interval is examined in terms of probabilities of U or SSS. If the probability measure for U exceeds an empirically determined threshold, the algorithm accepts the undersensing hypothesis. Thereafter, the pacemaker responds on the assumption that undersenses have occurred and are occurring. Likewise, if the probability measure is less than an empirically chosen threshold corresponding to SSS, the pacemaker accepts the Sick Sinus Syndrome hypothesis and is enabled to respond appropriately. If neither hypothesis is initially accepted, the test continues or is repeated until one or the other hypothesis can be accepted, or until it is concluded that the test is indeterminate, such that neither hypothesis can be accepted.

Figure 5A:
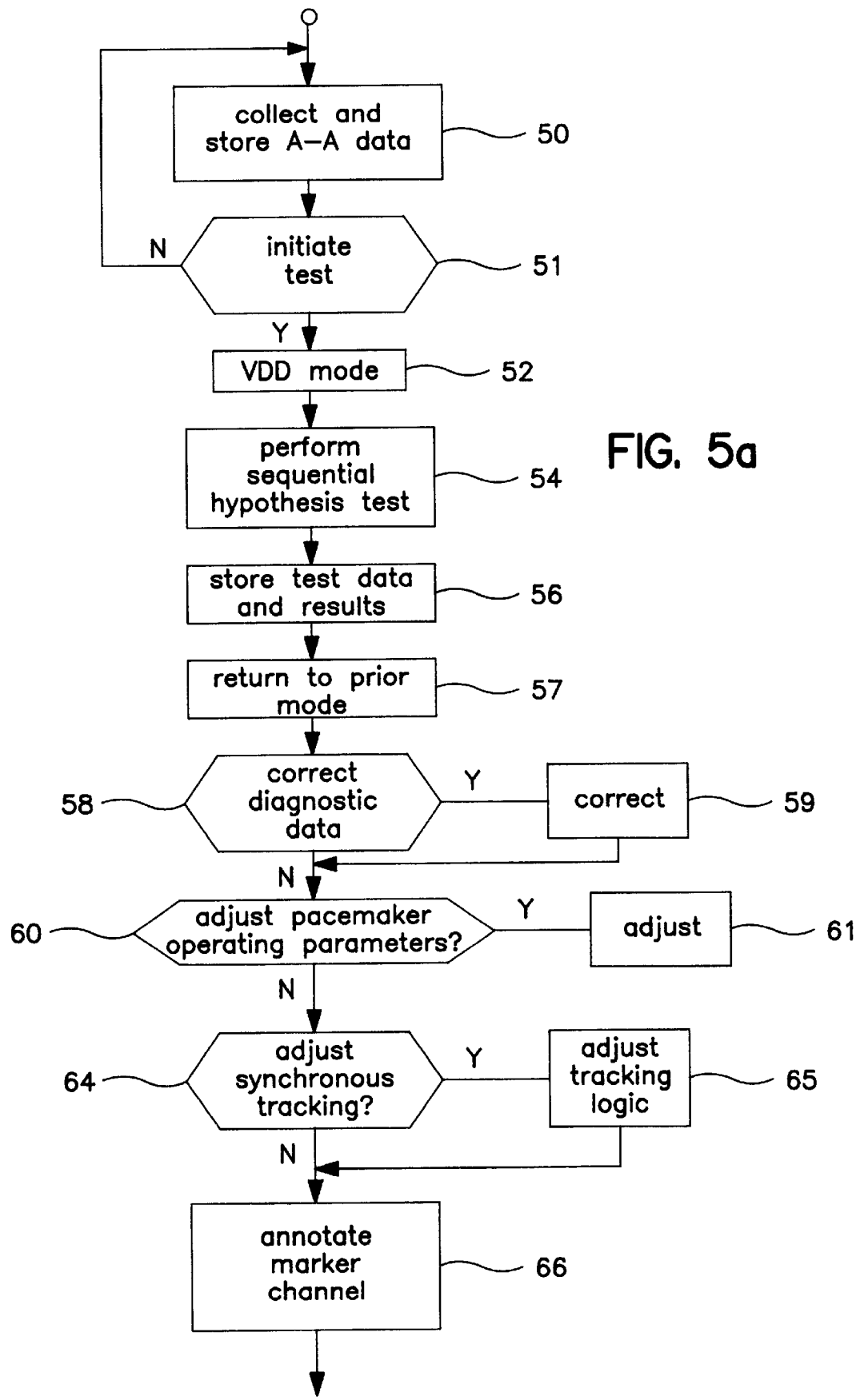
FIG. 5(a) is a flow diagram illustrating the method used to detect atrial undersensing.

Referring to FIG. 5A, there is shown a flow diagram of the basic steps for setting up and performing the sequential hypothesis test, and pacemaker options for responding to the test. At 50, the step of data collection is illustrated. Various amounts of time can be selected, we prefer about 5 minutes, but the reader should know that this period of time is not critical. In order to perform the statistical analysis of the preferred test algorithm, an accurate statistical measure of ongoing heart rate is required. Thus, in employing this embodiment, the A—A interval data is first collected, preferably on a continuous and ongoing basis, and the statistical mean and variance are calculated for normal sinus rhythm (NSR) and for those intervals that appear to be a SSS rhythm but which may be undersensing. The moving average data concerning atrial heart rate, or A—A interval, is taken over a long period of time so that statistically valid data is available at the time of undertaking the test. At 51, it is determined whether a test should be initiated. For example, the test may be initiated automatically in response to detected long A—A intervals, or can be initiated by a physician who programs the pacemaker to initiate the test. Alternately, the test can be automatically initiated periodically, e.g., every day or every twelve hours.

Once a decision is made to initiate the test, regardless of the reason found to be sufficient in the embodiment desired, if the device is a pacemaker, the mode is adjusted to VDD mode, as shown at step 52. In this mode, sensing of A—A intervals is not interrupted by delivered pace pulses. Other steps, such as minimizing PVARP, may be undertaken as a matter of choice for the particular pacemaker being utilized. After going to the VDD mode shown at 52, the sequential hypothesis test is undertaken at 54. The details of this test are set forth in relation to FIG. 5(b). The test results are stored at step 56, such that the pacemaker knows whether the hypothesis of either undersensing or sick sinus syndrome has been accepted. At this time, the pacemaker is also placed back in the DDD mode, if that is where it had been operating prior to the test. After this, a plurality of different responses may be enabled. At 58, it is determined whether the collected diagnostic data should or could be corrected based upon determination of U or SSS. Thus, a programmer or device based algorithm can interpret diagnostic data collected and stored in the pacemaker, and modify or correct such data based on the interpretation of missed events due to either U or SSS. If such a correction is to be undertaken, the implanted medical device or pacemaker performs this at step 59. At 60, it is determined whether the IMD or pacemaker is programmed to adjust any operating parameters in view of the test results. If yes, at step 61 one or more selected operating parameters may be adjusted. For example, the atrial sense amplifier sensitivity may be adjusted in an attempt to correct for undersensing. If the SSS hypothesis has been accepted, the pacemaker may respond by adjusting the lower rate limit, in order to enable sensing of more of the long atrial intervals. At 64, it is determined whether the pacemaker is to be adjusted for improved synchronous tracking. If yes, at 65 the tracking logic is changed based upon the accepted hypothesis, e.g., the logic is altered to assume undersense events, as discussed above in connection with FIG. 2C. Following this, as indicated at block 66, another option is to annotate the marker channel to indicate atrial undersensing episodes.

Referring now specifically to a preferred algorithm for hypothesis testing, recall that the premise is that a long interval in a series of m atrial intervals is either U or SSS. The algorithm is based upon the following two probabilities (where the A variables are the series of A—A intervals, where $A_1, A_2, \ldots A_m$ represent respective A—A intervals.):

$P(A_1, A_2, \ldots A_m|H_0)$ which is the probability of observing this series of atrial intervals assuming they result from undersensing, and $P(A_1, A_2 \ldots A_m|H_1)$ that is the probability of observing this series of atrial intervals, assuming they result from a sick sinus condition.

The ratio of these probabilities $P(A_1, A_2, \ldots A_m|H_0)$, and $P(A_1, A_2 \ldots A_m|H_1)$ is to be determined. Using Baye's equation, this probability ratio can be expressed as:

$$\frac{P(H_1|A_n, A_{n-1}, \ldots, A_{n-m})}{P(H_0|A_n, A_{n-1}, \ldots, A_{n-m})} = \frac{P(A_n, A_{n-1}, \ldots, A_{n-m}|H_1)P(H_1)}{P(A_n, A_{n-1}, \ldots, A_{n-m}|H_0)P(H_0)}$$

This is a form of the same expression that looks backward in time from $A_n$ to $A_m$. It should be recognized that the A intervals used in the calculation of the probabilities are not necessarily the same as the sensed intervals which are observed. Long intervals will be divided into a number of equally sized intervals based on the assumption that undersensing has occurred. The long intervals will be divided into shorter intervals that are as close as possible to the current average interval. These divided intervals will be used in both the numerator(SSS) and denominator(U) of the probability calculations. Sensed intervals that are not long (i.e., less than about 1.8 times the size of an average interval) will be used directly in the calculation of the probabilities. When a long interval is divided, exactly one of the resulting intervals will be used to replace that long interval. The division of the intervals will not be used to add intervals to the probability calculation. It will only adjust the size of an interval. The calculation of the probabilities may incorporate a combination of intervals that are adjusted in size and intervals that are exactly as observed.

A long interval, in our preferred embodiment, is defined as any interval substantially longer than a normal one, especially if it is approximately 1.8 times or larger, than a 'normal' or average sized one. This normal size can of course be adjusted for heart rate and other factors. The probabilities are evaluated only if there is a long interval, as otherwise the sinus rhythm is normal and there is no reason to carry out the test.

The hypothesis testing starts with a determination of the means and variances of the sick sinus rate and the normal sinus rate. Here, in determining the probability of undersensing, the premise is that the sinus rate is normal (NSR). For a series of intervals m=1, 2, 3 . . . M, the following determinations are made:

$$F_m \equiv \ln\frac{P(H_1|A_n, A_{n-1}, \ldots, A_{n-m})}{P(H_0|A_n, A_{n-1}, \ldots, A_{n-m})}$$

$$= m*\ln\frac{\sigma_0}{\sigma_1} + \frac{1}{2\sigma_0^2}\sum_{l=0}^{m}(A_{n-l}-\mu_0)^2 - \frac{1}{2\sigma_1^2}\sum_{l=0}^{m}(A_{n-l}-\mu_1)^2 + \ln\frac{P(H_1)}{P(H_0)}$$

$$F_m \equiv m*\ln\frac{\sigma_0}{\sigma_1} + \frac{1}{2\sigma_0^2}\sum_{l=0}^{m}[A_{n-l}-\mu(n)]^2 - \frac{1}{2\sigma_1^2}\sum_{l=0}^{m}[A_{n-l}-\mu(n)]^2 +$$

$$\ln\frac{P(H_1)}{P(H_0)}$$

$$T_1 = \ln\frac{1-\beta}{\alpha}$$

$$T_0 = \ln\frac{\beta}{1-\alpha}$$

Figure 5B:
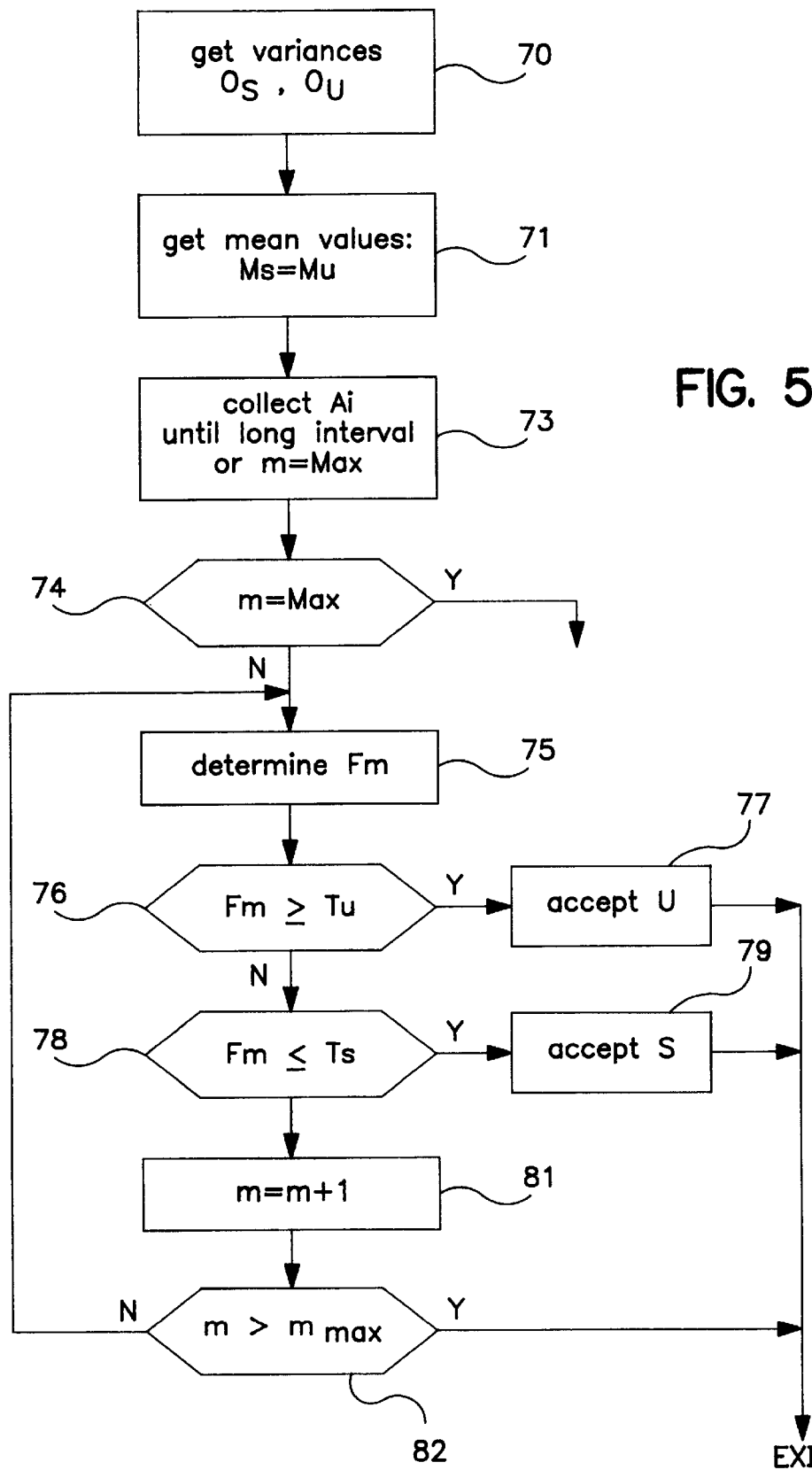
FIG. 5(b) is a flow diagram illustrating sequential hypothesis testing.

FIG. 5(b) is a flow diagram illustrating the main steps in carrying out the preferred algorithm for use in practice of this invention. The flow diagram of FIG. 5(b) represents details of block 54 indicated in FIG. 5(a). At 71, the running average of the mean interval, assumed to be same for SSS and U is obtained. It may be noted that in an alternative embodiment of this method, the mean calculations are performed in advance. This will be performed either prior to, or during, step 54 of FIG. 5a. In this case step 71, is eliminated from FIG. 5(b).

Returning now to FIG. 5(b), in step 74, the pacemaker looks for a long interval and collects A; for the last m intervals. Thus, this data represents the long interval plus a series of prior intervals. Next at step 75, the algorithm determines Fm, in accordance with the above equation, utilizing the variance, mean and $A_i$ data that have been collected. At 76, it is determined whether $F_m$ is greater than or equal to $T_u$. If yes, at 77 the pacemaker accepts the undersense hypothesis and sets a flag accordingly. If the answer at 76 is no, at 78 the pacemaker determines whether $F_m$ is less than or equal to $T_s$. If yes, pacemaker accepts the SSS hypothesis at 79, and sets an appropriate flag to control a pacemaker response. If the answer at 78 is no, at 81 m is incremented by 1, and at 82 it is determined whether m has exceeded a predetermined maximum value, e.g., 8 or 10. If no, the algorithm returns to block 75 and again determines $F_m$, this time utilizing the incremented set of $A_i$. In this way, the test is carried on until there is an acceptance of either test hypothesis, or the test has gone on to the point where m is greater than $m_{max}$, at which time the algorithm exists. Although not illustrated, the pacemaker may be programmed to wait for a short interval, e.g., 60 seconds, and repeat the test. The frequency and duration of the test are variables to be chosen by the physician.

FIGS. 6(a) and 6(b) are block diagrams that illustrates sensing of a heart rhythm, and are discussed in detail above.

Figure 7:
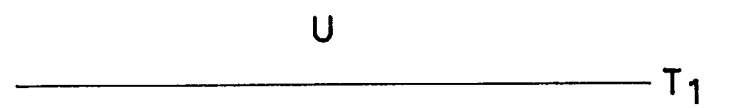
FIG. 7 is a graph of the decision boundaries for Undersensing (U) and Sick Sinus Syndrome (SSS).
Figure 7:
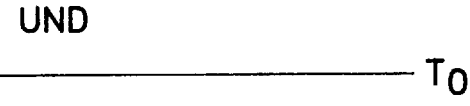

FIG. 7 is a graph of the decision boundaries for Undersensing (U) and Sick Sinus Syndrome (SSS). These diagrams illustrate the use of the threshold values $T_1$ and $T_0$ discussed above in reference to hypothesis testing. As indicated by FIG. 7, anything above the threshold $T_1$ is likely Undersensing and anything below threshold $T_0$ is likely to be a Sick Sinus Syndrome. Any time the value falls within the area between $T_0$ and $T_1$, no likelihood is indicated, and no determination of Undersensing or Sick Sinus Syndrome is made. Thus it can be seen that the values of $T_1$ and $T_0$ will have a great effect on the operation and outcome of the algorithmic process of determining whether we have a SSS or a U condition in a long interval.

The values of $T_0$ and $T_1$ can be set by choosing values for $\alpha$ and $\beta$. The values for $\alpha$ and $\beta$ should be small positive numbers less than 1. The smaller the value for $\alpha$ and $\beta$ the more specific the algorithm will be. The larger the value for a and b the more sensitive the algorithm will be. A typical value might be 2 e–2 with a range between 0.2 to 10 e–5. Decreasing $\alpha$ will raise the upper threshold while not significantly affecting the lower threshold. Decreasing $\beta$ will lower the lower threshold while not significantly affecting the upper threshold. It should be noted that there is no physical interpretation to the values.

Figure 8:
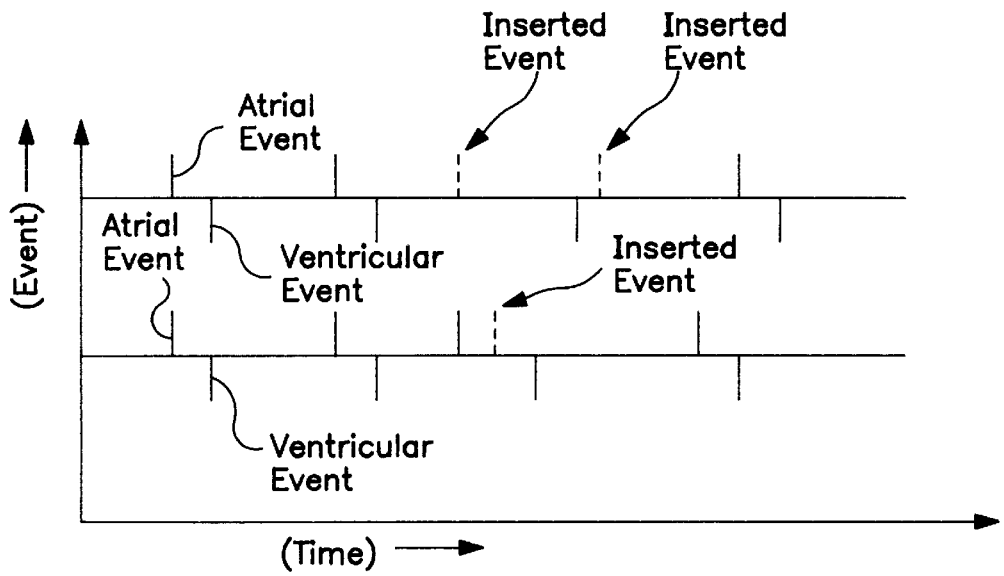
FIG. 8 is a timing diagram illustrating potential insertion points within a long atrial interval.
Figure 9:
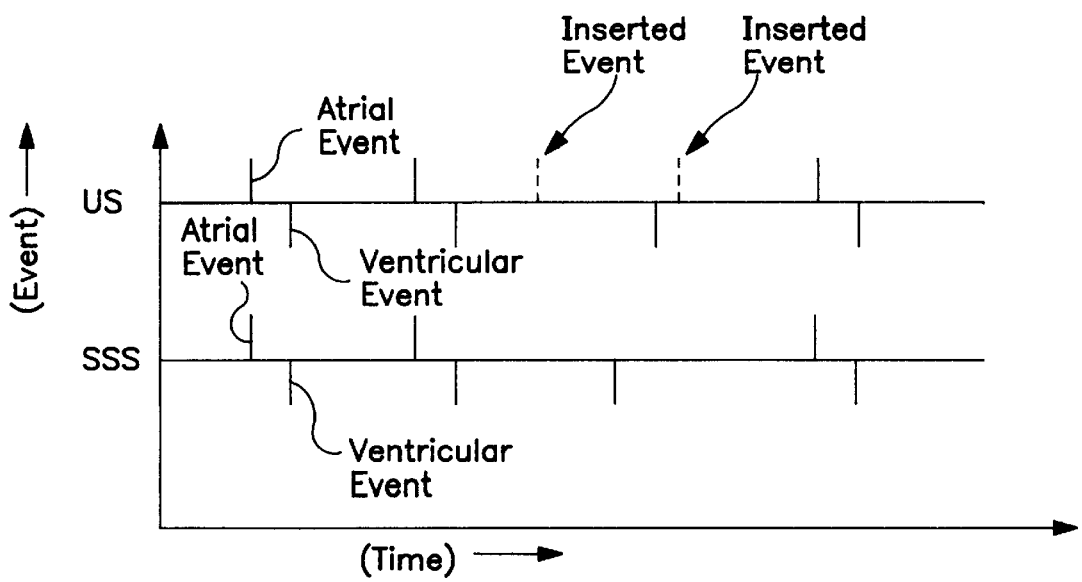
FIG. 9 is a timing diagram illustrating potential insertion points within a long atrial interval given the assumptions of Undersensing (U) and Sick Sinus Syndrome (SSS).

FIG. 8 is a timing diagram illustrating potential insertion points within long atrial intervals. Although the long sensed intervals are close, they result in a different number of inserted events, so in the preferred embodiment the inserted intervals are closest to the average interval size.

Inserted intervals are only used in calculating the probabilities for U and SSS. The running average mean is the same for both U (normal sinus rhythm) and SSS. It is updated as described in the pseudo-code explained below. The variance is not updated dynamically, in the preferred embodiments, being set in advance and remaining the same value. The variance used for SSS must be greater than the variance used for the expected normal sinus rhythm underlying the U hypothesis. Useful values for predetermined variances were found in a range around 100 ms for normal sinus rhythm and 250 ms for SSS.

It should be noted that the invention could be useful for Ventricular intervals that are missing as well, but sensing is currently better in the ventricle and the problem is therefore not a major medical issue.

If the current sensed interval is greater than about 2× the current average interval, suspected events will be inserted within sensed interval. The number of inserted events will depend on the size of the sensed interval. The larger the sensed interval the more events will be inserted. The inserted events are evenly spaced within the sensed interval and the size of the resulting interval will be that which is closest to the current average sensed interval.

The average sensed interval will be referred to as <a> and the current sensed interval will be referred to as A. We can define a variable n that is the number of whole average intervals that fit within the current sensed interval. The number of intervals that are inserted will be either n or n+1. If we divide A by n and then subsequently divide A by n+1, the resultant which is closest to <a> will determine whether we should insert n or n+1 intervals.

In the case where the sensed interval is 3.1× the size of the average interval we would insert either 2 or 3 suspected events (resulting in 3 or 4 intervals). If we insert 2 events then the size of the resulting intervals is (3.1/3)*<a> or 1.033*<a>. If we insert 3 events then the size of the resulting intervals is (3.1/4)*<a> or 0.775*<a>. Therefore inserting 2 events will result in intervals that are closest to the current average interval.

When determining which divided interval is closest to the current average interval, a distance measure is used. The distance measure is not critical to the algorithm (within reason). A percent difference or absolute difference could be used effectively. The type of difference measure should only affect the number of events that are inserted when the current sensed interval is not close to an even multiple of the average interval (i.e. A=3.5<a>).

The results of this procedure are used in calculating the relative probability of SSS or U when a long interval occurs. The inserted intervals are used in calculating the probability of SSS and U intervals.

It should be noted that even though the division of a long interval may result in many inserted intervals, only one of these inserted intervals is used in the calculation of the probability of SSS and U.

We apply these determinations through what can most simply be described as a do loop in general form through the following pseudocode:

```
μ(0) = A₀;
n = 1;
do
    {
    if (Aₙ ≤ μ(n − 1)) then μ(n) = μ(n = i) − 23ms;
    else μi(n) = μ(n − 1) + 8ms;
    n = n + 1;
    }
decision = undecided;
m = 1;
while(decision = undecided & m < max_m)
    {
    evaluate(Fₘ);
    if(Fₘ > T₁)decision = H₁;
    else if(Fₘ < T₀) decision = H₀;
    else m = m + 1;
    }
end do
```

In the pseudo code the average interval is $\mu$, and the initial interval is $\mu(n-1)$ where it substitutes for, or is used as, the initial value for the average interval A. The max_m is the number of times the probability is evaluated before stopping a run of this code. $T_1$ is $T_u$ and $T_2$ is $T_s$. The constants 23 and 8 milliseconds bias the value of the running mean toward decreasing rather than increasing because undersensed intervals may tend to increase the running mean incorrectly. These are preferred values only, and the user could find other values of interest. It is also useful to note that the values 8 and 23 result from the basic timing interval value in the current device, and represent approximations of one and three clock periods, respectively. Thus these values represent the jitter in the resolution of the intervals as measured by the particular embodiment using the time base of 7.8125 milliseconds. Other values will be used for other devices as would be known to one of skill in this art.

The value of $F_m$ is then compared with $T_u$ and $T_s$, which are empirically chosen threshold values. The threshold for undersensing and sick sinus is determined on the basis of sensitivity and specificity requirements, and programmed into the pacemaker. If $F_m$> or= to $T_u$, then the undersensing hypothesis is accepted. If $F_m$ is <or= to $T_s$, then the sick sinus hypothesis is accepted. In the event neither of these situations is arrived at, (that is, $F_m$ is between $T_u$ and $T_s$) the algorithm is continued by evaluating $F_m$ with m+1. Thus, the sequential hypotheses testing repeatedly evaluates the series of atrial senses and determines whether either hypothesis can be accepted, each time including the latest A—A interval in the evaluation.

In a preferred form of the sequential hypothesis test algorithm of this invention, it is assumed that the mean heart rate is not constant, such that the statistics are continually changing. Thus, in order for the algorithm to work properly, an accurate measure of the current heart rate is required. This is why the mean heart rate is calculated as a moving average, as discussed in relation to FIG. 5(a). It is assumed that the mean heart rates for the sick sinus syndrome and for normal sinus rhythm hypothesis are the same.

Basically, the algorithm enables discriminating between SSS, and undersensing in the presence of NSR, because NSR has a steady rate and SS does not. When a long atrial interval occurs, the algorithm looks at the current interval and a plurality of previous interval lengths. If the previous intervals are close to the mean rate, and the long interval is close to being a multiple of the mean rate, the long interval is likely to be classified as an undersense. Note that the previous intervals being evaluated may be also be multiples of the mean rate, and the algorithm allows for this.

Figure 10:
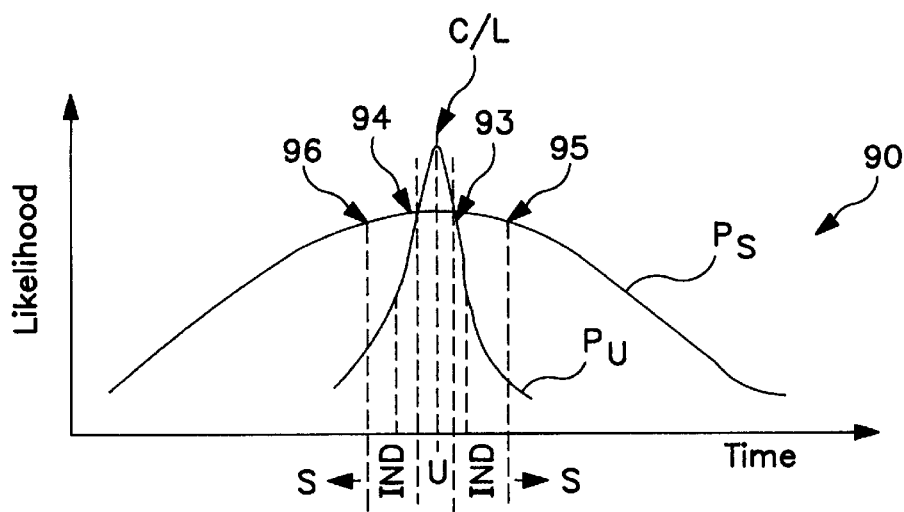
FIG. 10 is a probability distribution curve representing the probabilities of U or SSS based on the Atrial-event-to-Atrial-event (A—A) interval.

FIG. 10 is a probability distribution curve representing the probabilities of U or SSS based on the Atrial-event-to-Atrial-event (A—A) interval. Note that the probability distribution curves for Sick Sinus Syndrome events Ps and for Undersensing (missing a normal sinus rhythm event) Pu share a common center that is the mean atrial interval.

Figure 11:
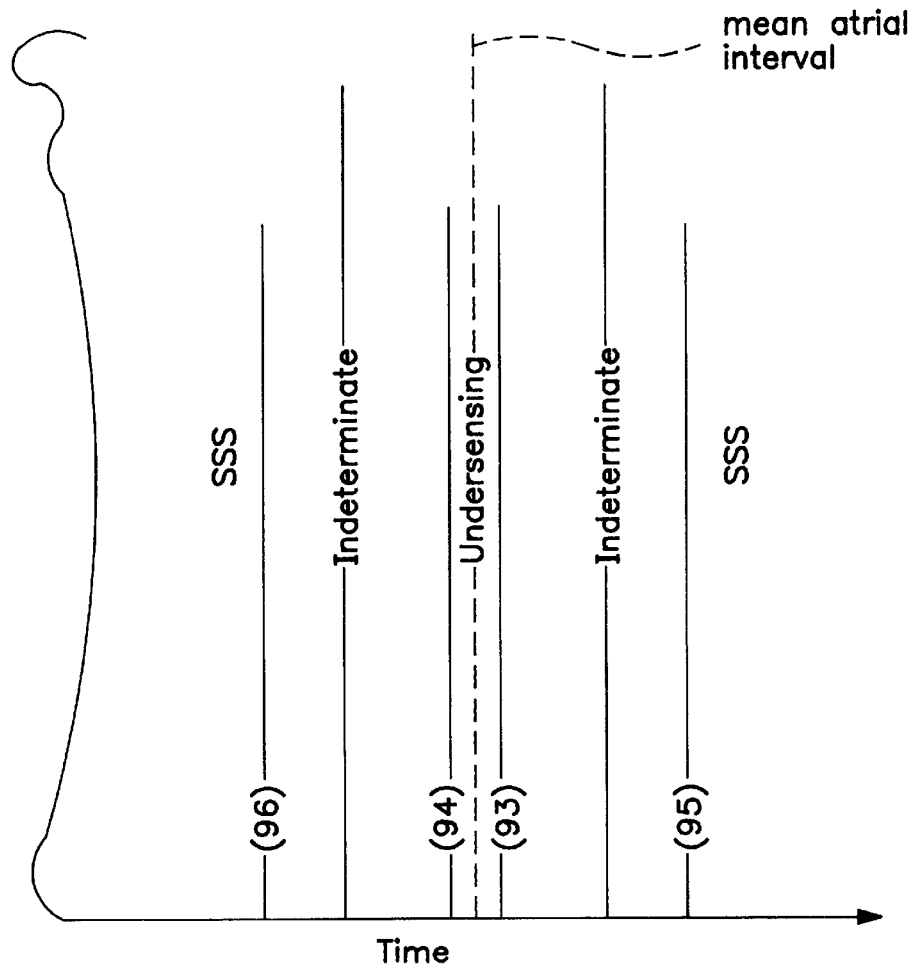
FIG. 11 is an expanded top-level view of the probability distribution curve of FIG. 10.

FIG. 11 is an expanded top-level view of the probability distribution curve of FIG. 10. FIG. 11 illustrates the ranges of interval times that would widely give rise to the indicated state of U or SSS. FIG. 11 is related to FIG. 7 in that FIG. 11 indicates decision boundaries in the time interval space and FIG. 7 indicates decisions boundaries after they have been transposed through the calculation of the likelihood ratio.

The probability distribution of FIGS. 10 and 11 utilize the divided interval sizes for the values along the abscissa as described above. The use of divided intervals can be thought of as folding of the sensed interval size (when it is a long interval) to be within a range close to the mean interval size. Thus the area between this and intersection points 93 and 94 of FIG. 10 indicate greater likelihood of the U hypothesis for a given atrial interval. Between points 93 and 95, the probability of a SSS or a U hypothesis being correct is indeterminate or undetermined by our algorithmic process as it is between points 94 and 96. On the other side of points 95 and 96, we have some greater confidence that the atrial interval for such a length of time is caused by a sick sinus condition and accordingly the algorithm will classify it as such.

Although a preferred embodiment of a specific algorithm has been disclosed, it is to be understood that variations on the statistical approach may be utilized within the scope of this invention. The important feature of the invention is to perform a statistical analysis by which to determine the likelihood that a long atrial interval is due to pacemaker undersensing, or some other cause that we attribute to sick sinus syndrome.

Applicants' invention can also be used in conjunction with reprogramming of pacer parameters. Current sensing implementations could adjust sensitivity threshold and/or sensing polarity to improve sensing performance. More advanced sensing techniques which rely on morphological analysis may also adjust parameters to recognize that events were missed and improve sensing. If the undersensing was due to lower rate timing in a VDD or DDD device, and maintenance of AV synchrony was important, the lower rate could be lowered to permit synchronization with the P-waves.

Applicants' invention can also be used in conjunction with DDD/R applications. A dual chamber pacemaker that delivers atrial paces may complicate detection of undersensing by interrupting what would be long atrial intervals at multiples of the atrial rate mean. To correct this problem, the algorithm could count atrial pacing as though a long interval had occurred. The device could then alternate in a mode that alternates between DDD and VDD on each beat, providing ventricular pacing at the lower rate and atrial pacing at ½ that rate. Alternatively, and preferably, following a determination that undersensing has missed an atrial beat, the pacemaker IMD could deliver a ventricular pace pulse timed to the missing atrial sense at whatever the IMD has determined is the appropriate atrioventricular escape interval, thus yielding a device with forced AV-synchronous pacing in the absence of atrial sensing. A triggering program associated with and able to influence the ventricular escape interval can be easily fashioned to accommodate this need by any skilled practitioner in this art.

The invention described herein could be used with any electrode system for sensing atrial electrical changes, including, for example, the subcutaneous electrode array as taught in Bennet et al, U.S. Pat. No. 5,331,966, incorporated by reference, which is not even linked directly to atrial tissue, or even with external electrodes for another example, or with any device that senses atrial contractions and where the A—A interval may be determined inaccurately but could be enhanced in accuracy by use of the techniques taught herein.

Accordingly, the invention's ambit is considered limited only by the following appended claims.

What is claimed is:

1. An implantable medical device having atrial sensing means for sensing physiologic atrial signals and for producing an atrial sensed event signal responsive thereto, comprising:

atrial interval means for determining atrial interval values between said atrial sensed event;

storage means for storing values of successive said atrial interval values;

data means for obtaining statistical data representative of a variance of a mean value of said atrial intervals;

detecting means for detecting an occurrence of a statistically long one of said atrial interval values within said stored values; and evaluating means for assigning, based on said statistical data, a probability value indicative of whether said long one of said atrial intervals was due to undersensing, and for producing a signal representing said assigned probability value for said long one of said atrial intervals.

2. The implantable medical device as set forth in claim 1, wherein said evaluating means comprises means for performing sequential hypothesis testing based on a series of said atrial interval values.

3. The implantable medical device as set forth in claim 1, wherein said data means comprises determining means for determining said mean value of said atrial interval values.

4. The implantable medical device as set forth in claim 1, wherein said storage means stores ventricular escape intervals, and further comprising:

an implantable pulse generator housed within said device;

a medical electrical lead for providing timed electrical stimulation pulses to ventricular cardiac tissue from said implantable pulse generator, said timed electrical stimulation pulses based on said ventricular escape intervals stored by said storage means; and synchronizing means enabled if said probability value is indicative of undersensing, said synchronizing means for synchronizing delivery of said timed electrical stimulation pulses with an atrial sinus beat which is not sensed due to undersensing by controlling said ventricular escape intervals.

5. The implantable medical device as set forth in claim 1, wherein said evaluating means further comprises means for assigning a probability value indicative of whether said long one of said atrial intervals was caused by an occurrence of sick sinus syndrome.

6. The implantable medical device as set forth in claim 1, wherein said evaluating means comprises means for initiating a test for determination of undersensing, said means for initiating a test comprising means for placing said implantable medical device in a VDD mode.

7. The implantable medical device of claim 6, and further comprising a flag to indicate whether to test for undersensing, and wherein said means for initiating a test additionally comprises means for determining whether said flag is in a predetermined state.

8. A testing system, for use in an implantable medical device, said implantable medical device having sensing means for sensing a patient's atrial heartbeat signals, said testing system to determine whether said sensing means is missing atrial senses due to undersensing, said testing system comprising:

atrial interval means for continually determining an interval time values between atrial senses;

data means for obtaining a mean value for said interval time values, and for determining from said mean value a nsr variance value for a normal sinus atrial rate and a sss variance value for a sick sinus atrial rate;

determining means for determining a statistically long atrial interval and for determining from said nsr variance value and said sss variance value and said mean value a measure of probability that said long interval was due to undersensing; and comparison means for comparing said measure with a predetermined undersense threshold to determine whether said long interval was due to undersensing.

9. The system as described in claim 8, comprising means for continuing said determination by said testing system when said comparing does not determine whether said long interval was due to undersensing.

10. A method carried out by a dual chamber pacemaker for determining when atrial undersensing is occurring, comprising:

sensing atrial signals and determining from said sensed atrial signals atrial intervals between said sensed atrial signals;

storing values of said atrial intervals;

obtaining statistical data representative of said stored atrial intervals, said statistical data including variance values for a normal sinus rate and a sick sinus rate;

detecting an occurrence of a statistically long atrial interval;

determining, based on said long atrial interval, said stored atrial intervals and said statistical data, whether said long interval was due to atrial undersensing.

11. A method as set forth in claim 10 further comprising coordinating delivery of a ventricular pacing stimulation based on the determining step.

12. An implantable medical device, comprising:

atrial sense means for sensing atrial signals from a patient;

long interval means for determining when there is a long interval between two successive atrial signals;

undersense means for determining when a said long interval is to be classified as an undersense, said undersense determining means comprising:

first probability means for determining a first probability that said long interval was due to undersensing by said atrial sense means;

second probability means for determining a second probability that said long interval was due to patient sick sinus syndrome; and classifying means for classifying said long interval as an undersense based on a function of said first and second probabilities.

13. An implantable medical device as set forth in claim 12, further comprising means for assuming that one of said atrial signals occurred within said long interval that is classified as an undersense.

14. An implantable medical device as set forth in claim 13 and further comprising means for providing ventricular stimulation to a patient's heart in timed relation to an undersense.

15. A method for use in an implantable device for determining whether long atrial intervals included between atrial beats of a sensed atrial signal are a result of one of undersensing a absence of atrial beats, the method comprising the steps of:

a.) calculating an average time interval between said atrial beats of said sensed atrial signal;

b.) a long atrial interval between two successive ones of said atrial beats that is longer than said average time interval by a predetermined value;

c.) calculating probability data descriptive of sick sinus syndrome rates and probability data indicative of undersensing rates based on said average time interval; and d.) determining, based on said probability a whether said long atrial interval is due to one of sick sinus syndrome, undersensed normal sinus rate, and a cause that can not be determined.

16. The method of claim 14, wherein step b.) includes the step of dividing said long atrial interval into portions and selecting a predetermined one of said portions for use as said long atrial interval in step d.).

17. The method of claim 16, and further including the step of modifying said average time interval based on the length of said predetermined one of said portions obtained in step b.).

18. The method of claim 15, wherein the implantable device further delivers cardiac pacing pulses, and further including the step of adjusting the rate of said cardiac pacing pulses based on the determination made in step d.).

19. An implantable medical device, comprising:

an atrial signal sensor to sense atrial signals;

a processor coupled to said atrial sensor to a.) calculate a mean value for intervals between successive ones of said atrial signals, to b.) determine whether any said interval between successive ones of said atrial signals is indicative of a long atrial interval, and to c.) calculate a variance from said mean value for each said long atrial interval; and a storage device coupled to said processor to store probability distribution signals descriptive of the rate of said atrial signals, wherein said processor utilizes said probability distribution signals for determine whether said variance is indicative of one of an undersensed normal atrial rate and sick sinus syndrome.

20. The implantable medical device of claim 19, and further including:

an output amplifier circuit to deliver a pacing signal; and a timer circuit coupled to said output amplifier circuit and to said processor, said timer circuit to adjust said pacing signal based on whether said processor makes a determination that said variance is indicative of one of an undersensed normal atrial rate and sick sinus syndrome.

21. The implantable medical device of claim 19, and further including processing means for dividing each said long atrial interval into portions and using a predetermined one of said portions to re-calculate said mean value.

22. The implantable medical device of claim 21, and further including means for adjusting said probability distribution signals stored in said storage device based on a re-calculated mean value.

* * * * *

UNITED STATES PATENT AND TRADEMARK OFFICE
CERTIFICATE OF CORRECTION

PATENT NO.   : 6,129,745
DATED         : October 10, 2000
INVENTOR(S)  : Sun et al.

It is certified that error appears in the above-identified patent and that said Letters Patent is hereby corrected as shown below:

Column 16, claim 1,
Line 24, "sensed event" should read -- sensed event signals --

Column 18, claim 16,
Line 23, "The method of claim 14" should read -- The method of claim 15 --

Signed and Sealed this

Sixth Day of November, 2001

*Attest:*

NICHOLAS P. GODICI
*Attesting Officer*    Acting Director of the United States Patent and Trademark Office